US 10,980,520 B2
(12) United States Patent
Green et al.

(10) Patent No.: US 10,980,520 B2
(45) Date of Patent: Apr. 20, 2021

(54) URINE SAMPLING VESSEL

(71) Applicant: Green Panther Ventures, Huntington Beach, CA (US)

(72) Inventors: Matt S Green, Huntington Beach, CA (US); Joseph Daniel Massam, Langhorne, PA (US)

(73) Assignee: Green Panther, LLC, Irvine, CA (US)

(*) Notice: Subject to any disclaimer, the term of this patent is extended or adjusted under 35 U.S.C. 154(b) by 84 days.

(21) Appl. No.: 15/298,138

(22) Filed: Oct. 19, 2016

(65) Prior Publication Data

US 2017/0143314 A1 May 25, 2017

Related U.S. Application Data

(60) Provisional application No. 62/319,471, filed on Apr. 7, 2016, provisional application No. 62/243,383, filed on Oct. 19, 2015.

(51) Int. Cl.
A61B 10/00 (2006.01)
A61B 10/02 (2006.01)

(52) U.S. Cl.
CPC .... A61B 10/007 (2013.01); A61B 2010/0216 (2013.01)

(58) Field of Classification Search
CPC .................................................. A61B 10/007
See application file for complete search history.

(56) References Cited

U.S. PATENT DOCUMENTS

| 4,014,322 A | * | 3/1977 | Shah | A61B 10/007 600/573 |
| 4,326,481 A | * | 4/1982 | Gruss | A01K 1/0107 119/171 |
| 4,485,824 A | | 12/1984 | Koll | |
| 4,596,157 A | | 6/1986 | Laauwe | |
| 4,653,510 A | | 3/1987 | Koll | |
| 4,707,450 A | | 11/1987 | Nason | |
| 4,961,432 A | | 10/1990 | Guirguis | |
| 4,978,504 A | | 12/1990 | Nason | |
| 5,031,635 A | | 7/1991 | Koll | |
| 5,078,968 A | | 1/1992 | Nason | |
| 5,096,062 A | | 3/1992 | Burkardt et al. | |
| 5,129,402 A | | 7/1992 | Koll et al. | |
| 5,238,649 A | | 8/1993 | Nason | |
| 5,266,266 A | | 11/1993 | Nason | |
| 5,283,038 A | * | 2/1994 | Seymour | A61B 5/411 435/287.2 |
| 5,352,410 A | | 10/1994 | Hansen et al. | |
| 5,494,646 A | | 2/1996 | Seymour | |
| 5,504,013 A | | 4/1996 | Senior | |

(Continued)

FOREIGN PATENT DOCUMENTS

WO 2014124905 A1 8/2014
WO 2014163588 A1 10/2014
WO 2015159089 A1 10/2015

Primary Examiner — Daniel L Cerioni
Assistant Examiner — Raymond P Dulman
(74) Attorney, Agent, or Firm — Schott, P.C.

(57) ABSTRACT

A biological fluid sampling vessel may include a container portion having an opening and an interior for housing a urine sample therein. The vessel may further include a sampling portion that removably engages the container portion to close off the interior. The sampling portion may include a sampling wand configured for obtaining a sample.

8 Claims, 13 Drawing Sheets

(56) References Cited

U.S. PATENT DOCUMENTS

| | | |
|---|---|---|
| 5,523,055 A | 6/1996 | Hansen et al. |
| 5,869,003 A | 2/1999 | Nason |
| 5,881,596 A | 3/1999 | Tsuji et al. |
| 6,150,178 A | 11/2000 | Cesarczyk et al. |
| 6,241,689 B1 | 6/2001 | Chard et al. |
| 6,248,294 B1 | 6/2001 | Nason |
| 6,524,530 B1 | 2/2003 | Igarashi et al. |
| 6,821,788 B2 | 11/2004 | Cesarczyk |
| 7,098,040 B2 | 8/2006 | Kaylor et al. |
| 7,114,403 B2 | 10/2006 | Wu et al. |
| 7,294,502 B2 | 11/2007 | Eckermann et al. |
| 7,300,627 B1 | 11/2007 | Sun |
| 7,311,671 B2 | 12/2007 | Jung et al. |
| 7,618,591 B2 | 11/2009 | Slowey et al. |
| 7,833,169 B2 | 11/2010 | Hannon |
| 7,915,032 B2 * | 3/2011 | Ostrowski .......... A61B 10/0045 422/411 |
| 7,927,548 B2 | 4/2011 | Slowey et al. |
| 7,993,871 B2 | 8/2011 | Skiffington et al. |
| 8,025,851 B2 | 9/2011 | Slowey et al. |
| 8,226,906 B2 | 7/2012 | Saul |
| 8,273,305 B2 | 9/2012 | Slowey et al. |
| 8,696,595 B2 | 4/2014 | Sangha |
| 8,728,414 B2 | 5/2014 | Beach et al. |
| 8,871,155 B2 | 10/2014 | Wu et al. |
| 8,979,784 B2 | 3/2015 | Triva |
| 2004/0018634 A1 | 1/2004 | Hajizadeh et al. |
| 2004/0082078 A1 | 4/2004 | Lin et al. |
| 2004/0267181 A1 | 12/2004 | Tuite et al. |
| 2005/0119589 A1 * | 6/2005 | Tung .................. A61B 10/0045 600/584 |
| 2006/0142669 A1 | 6/2006 | Morimoto et al. |
| 2007/0299364 A1 | 12/2007 | Sangha |
| 2009/0024060 A1 | 1/2009 | Darrigrand et al. |
| 2009/0181451 A1 | 7/2009 | Slowey et al. |
| 2011/0087133 A1 | 4/2011 | Ching et al. |
| 2011/0144535 A1 * | 6/2011 | Guirguis ............ A61B 10/0051 600/573 |
| 2011/0165024 A1 | 7/2011 | Wu et al. |
| 2012/0067144 A1 | 3/2012 | Slowey et al. |
| 2012/0094303 A1 * | 4/2012 | Engel ................ A61B 10/0045 435/7.1 |
| 2013/0289443 A1 | 10/2013 | Kim et al. |
| 2015/0212081 A1 | 7/2015 | Catteruccia et al. |
| 2015/0268135 A1 * | 9/2015 | Hu .................. G01N 33/48714 73/864.33 |

\* cited by examiner

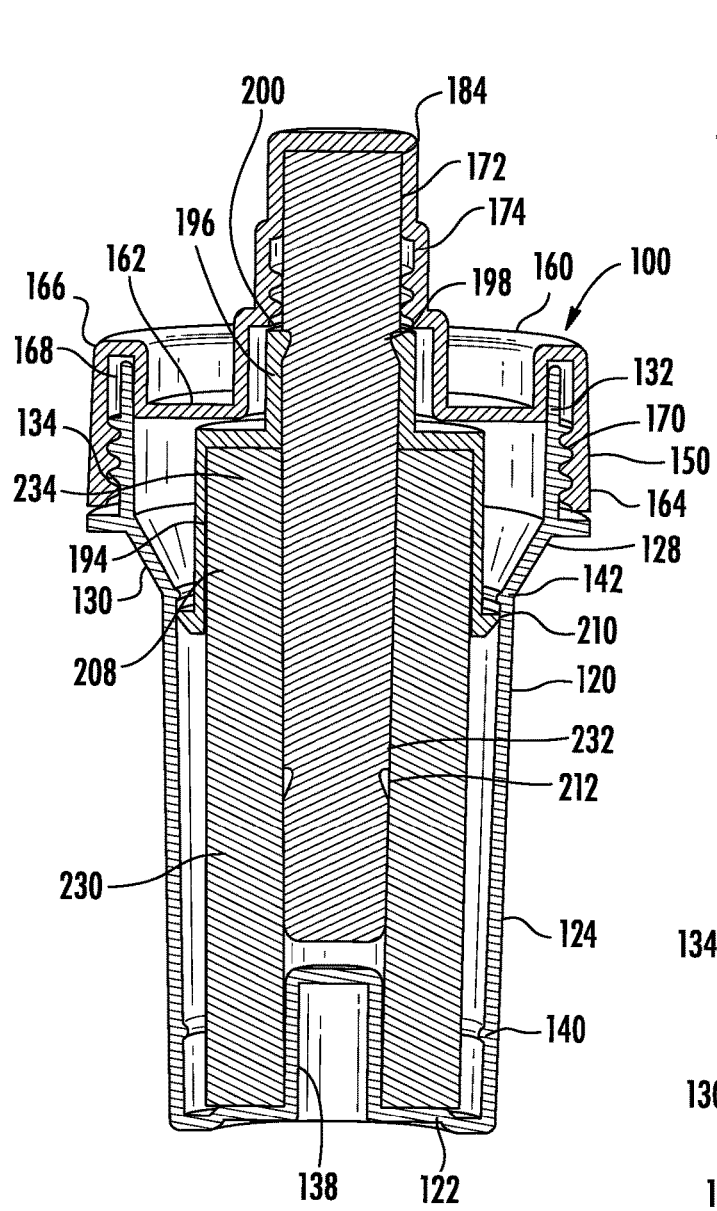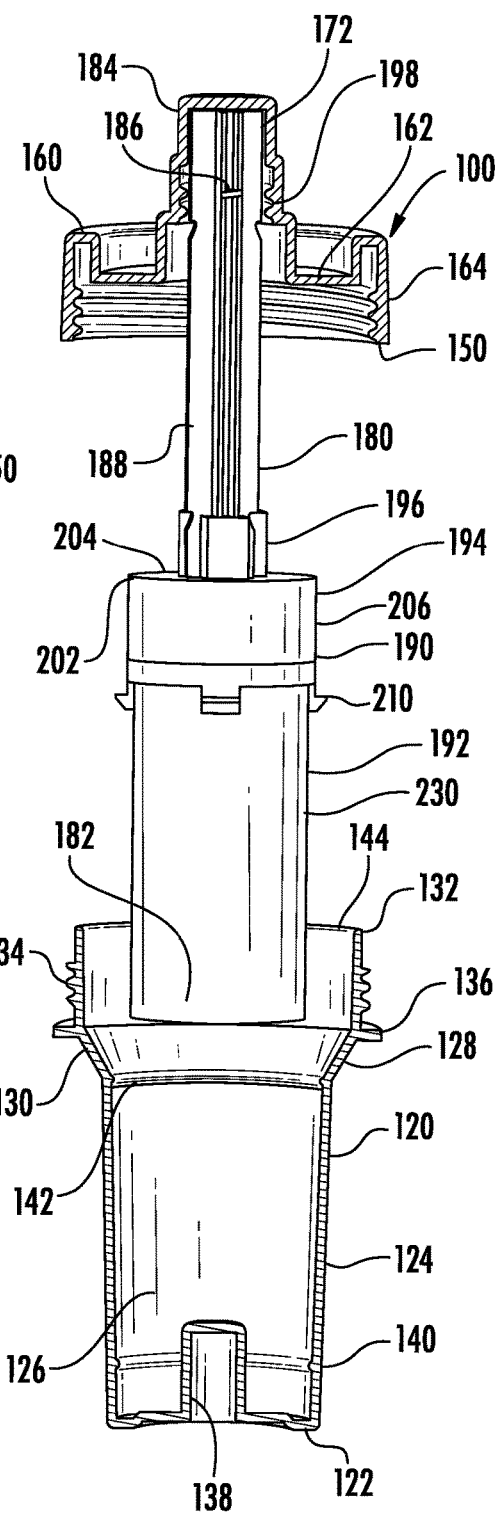
FIG. 1
FIG. 2

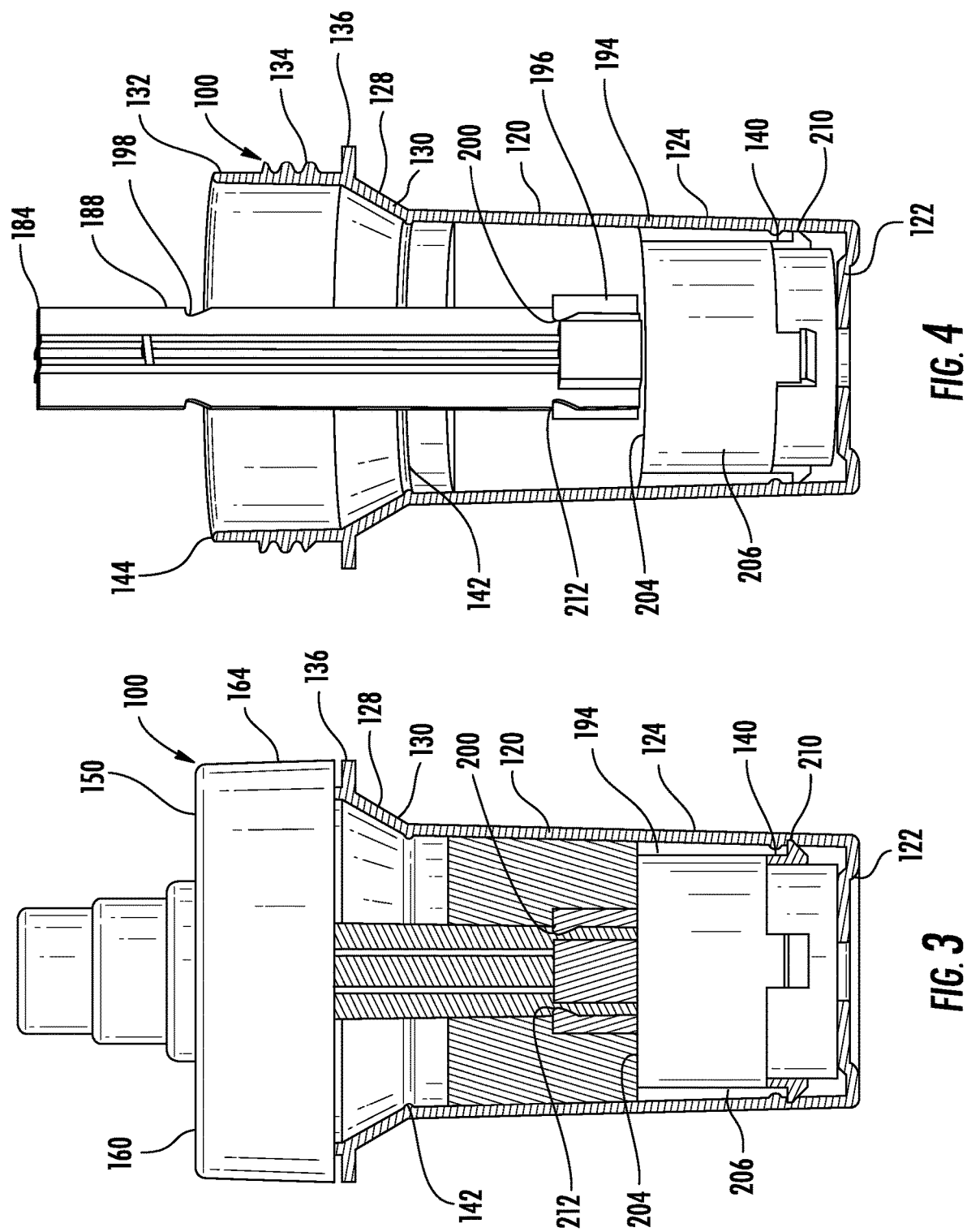

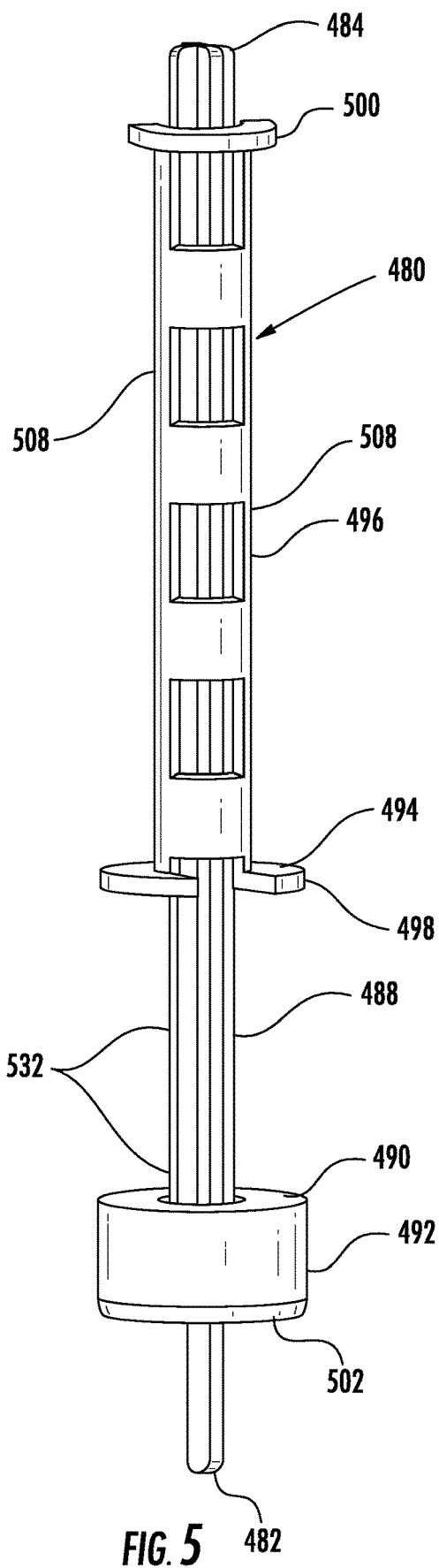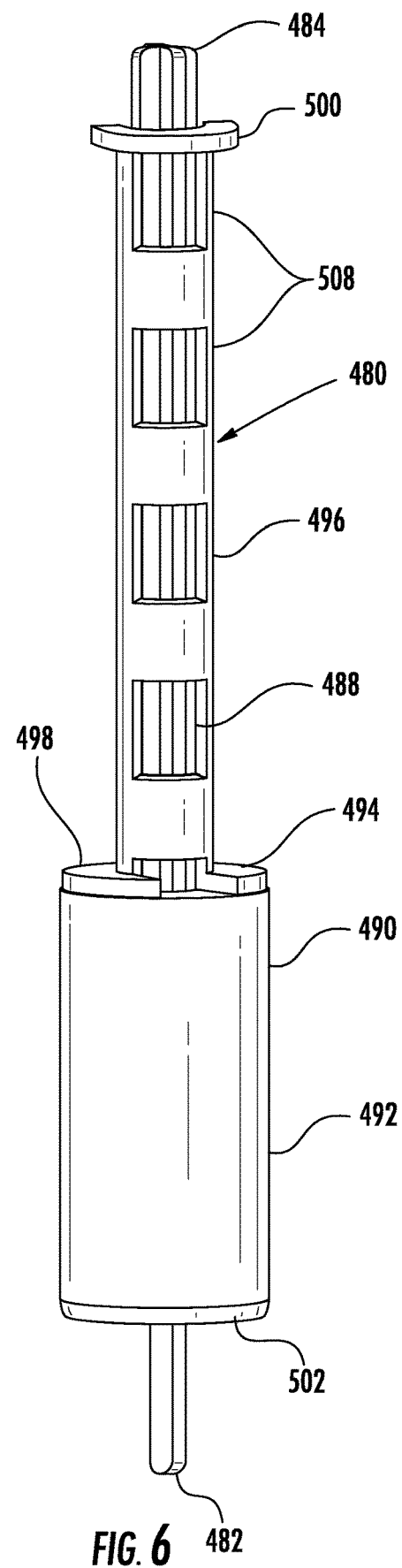

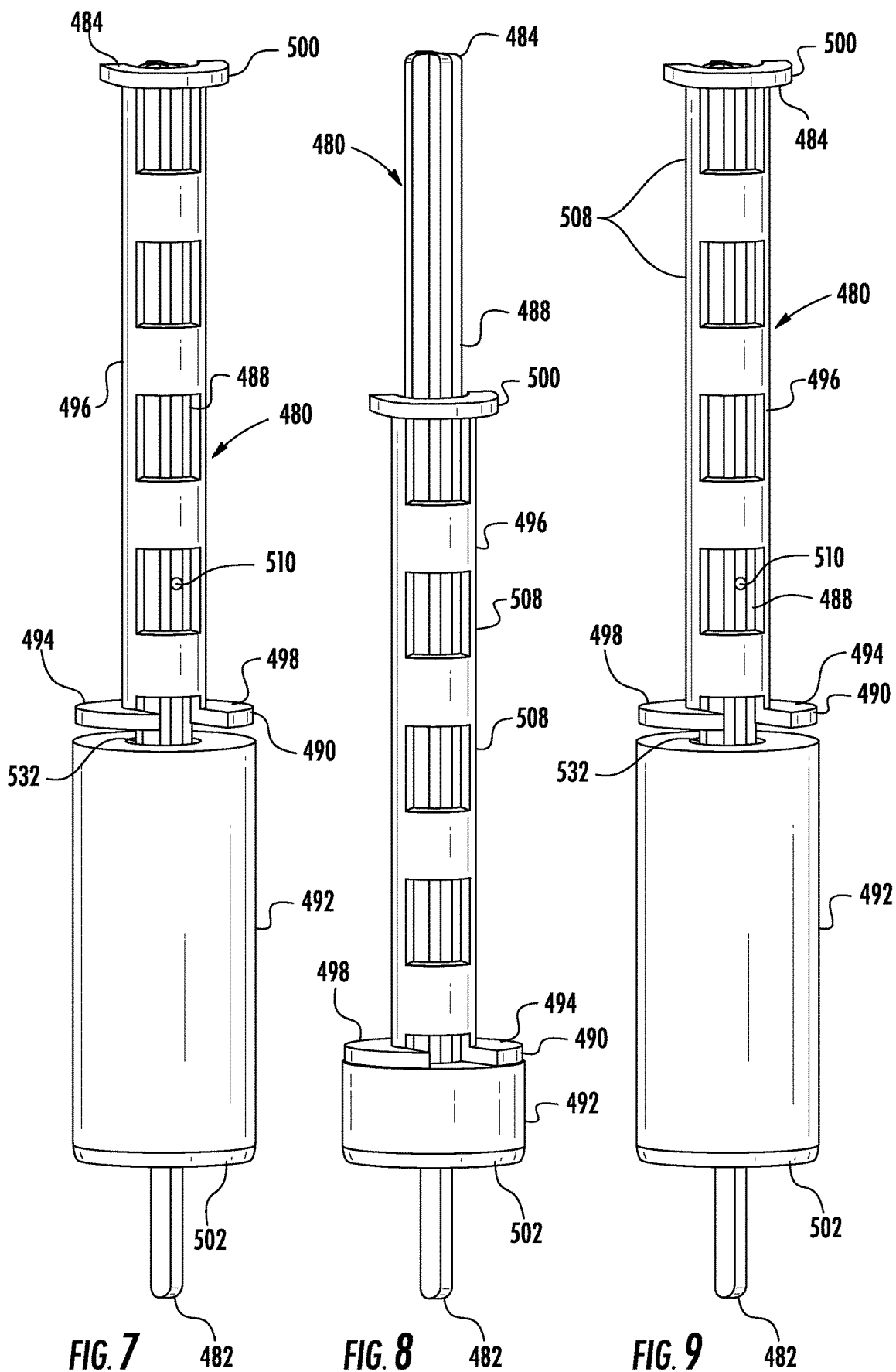

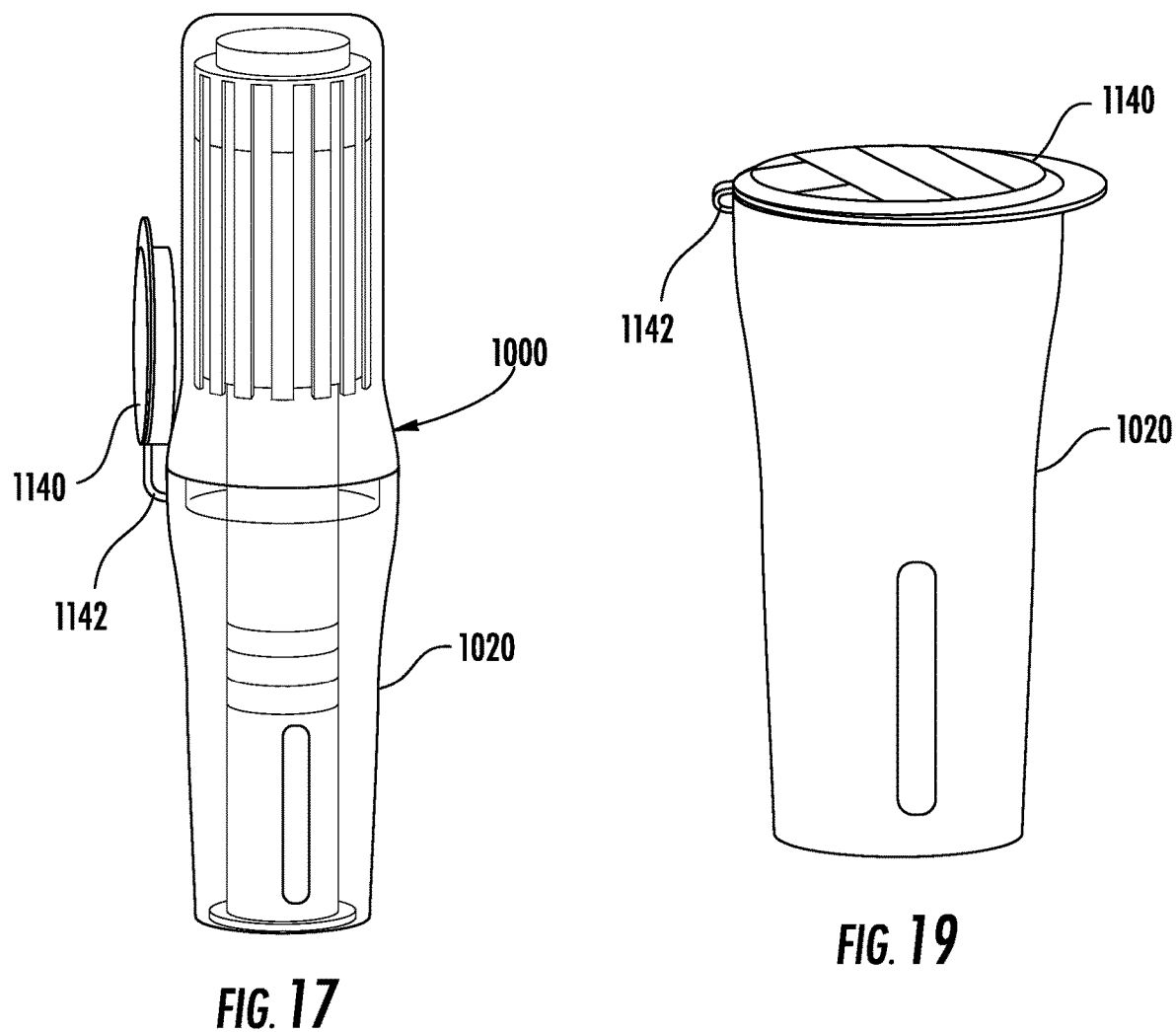

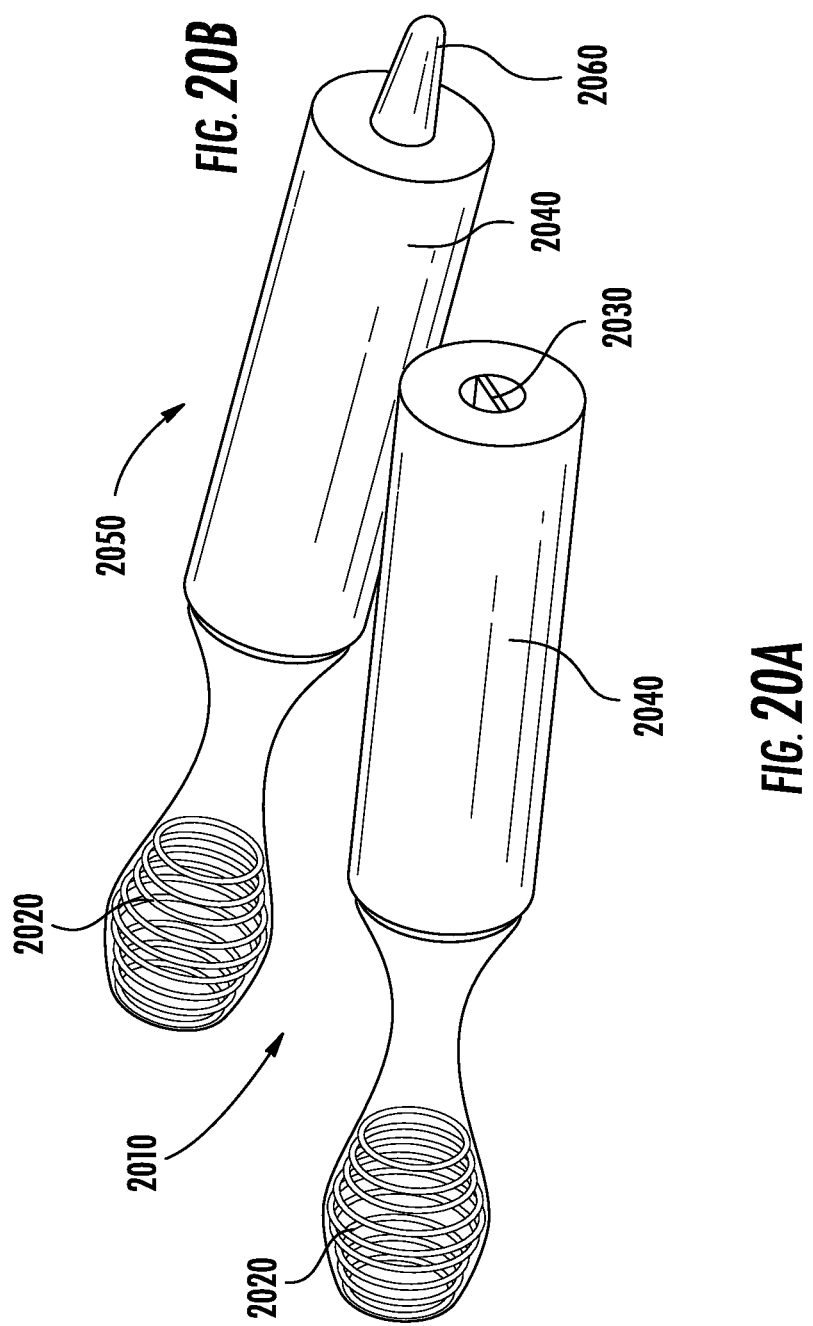

URINE SAMPLING VESSEL

BACKGROUND

Urinalysis has been used for over 6,000 years as a diagnostic tool for measuring health, testing for diseases, and monitoring their progression. Although Hippocrates is often credited with first recognizing the value of urine in analyzing the state of a person's physical well-being, evidence exists that ancient Sumerian, Babylonian and Hindu physicians assessed urine as part of their patient care. With advances in modern medicine have come improvements in urine collection and testing methods, and many devices exist today for the collection, testing, and transport of urine specimens. Even with this long history, challenges remain. Urine can be easily contaminated by bacteria during the collection process, rendering test results faulty or inaccurate. Contamination of a urine specimen can occur, for example, if a patient inadvertently touches the inside of the collection cup or cap. Given the traditional design of urine cups and their screw-on lids, urine samples are easily spilled by patients and healthcare workers, placing them at increased risk of exposure. And, as anyone who has ever given a urine sample can attest, they require self-administration but are awkward, at best, and messy, at worst, to execute.

SUMMARY OF THE EMBODIMENTS

A urine sampling vessel may include a container portion having an opening and an interior for housing a urine sample therein. The vessel may further include a sampling portion that removably engages the container portion to close off the interior. The sampling portion may include a sampling wand configured for obtaining a urine sample.

BRIEF DESCRIPTION OF THE DRAWINGS

FIG. 1 is a cross-sectional view of an embodiment of a urine sampling vessel in a closed pre-use position, with the sponge holder in a first, retracted position, prior to use for obtaining a urine sample.

FIG. 2 is a partial cross-sectional view of the vessel of FIG. 1, in an opened position and with the sponge holder in a second, extended position.

FIG. 3 is a partial cross-sectional view of the vessel of FIG. 1 in a post-use closed position, with the sponge holder in the extended position and the sponge in a compressed state, after use for obtaining a urine sample.

FIG. 4 is a partial cross-sectional view of the vessel of FIG. 1, with the lid removed therefrom.

FIG. 5 is a perspective view of an embodiment of a urine sampling vessel wand, with the sponge in a compressed state, prior to use for obtaining a urine sample.

FIG. 6 is a perspective view of the wand of FIG. 5, with the sponge in a saturated and fully expanded state, during the process of obtaining a urine sample.

FIG. 7 is a perspective view of the wand of FIG. 5, with the sponge in a partially compressed state.

FIG. 8 is a perspective view of the wand of FIG. 5, with the sponge in a compressed state to express a urine sample obtained.

FIG. 9 is a perspective view of the wand of FIG. 5, in a re-expanded state, after the urine sample has been expressed as shown in FIG. 8.

FIG. 17 is a perspective view of another embodiment of a urine sampling vessel, in a closed position.

FIG. 19 is a perspective of the container of the urine sampling vessel of FIG. 17, with the transport lid in a closed position.

FIG. 20A and FIG. 20B show alternate embodiments of the wand.

DETAILED DESCRIPTION OF THE EMBODIMENTS

Figure 10:
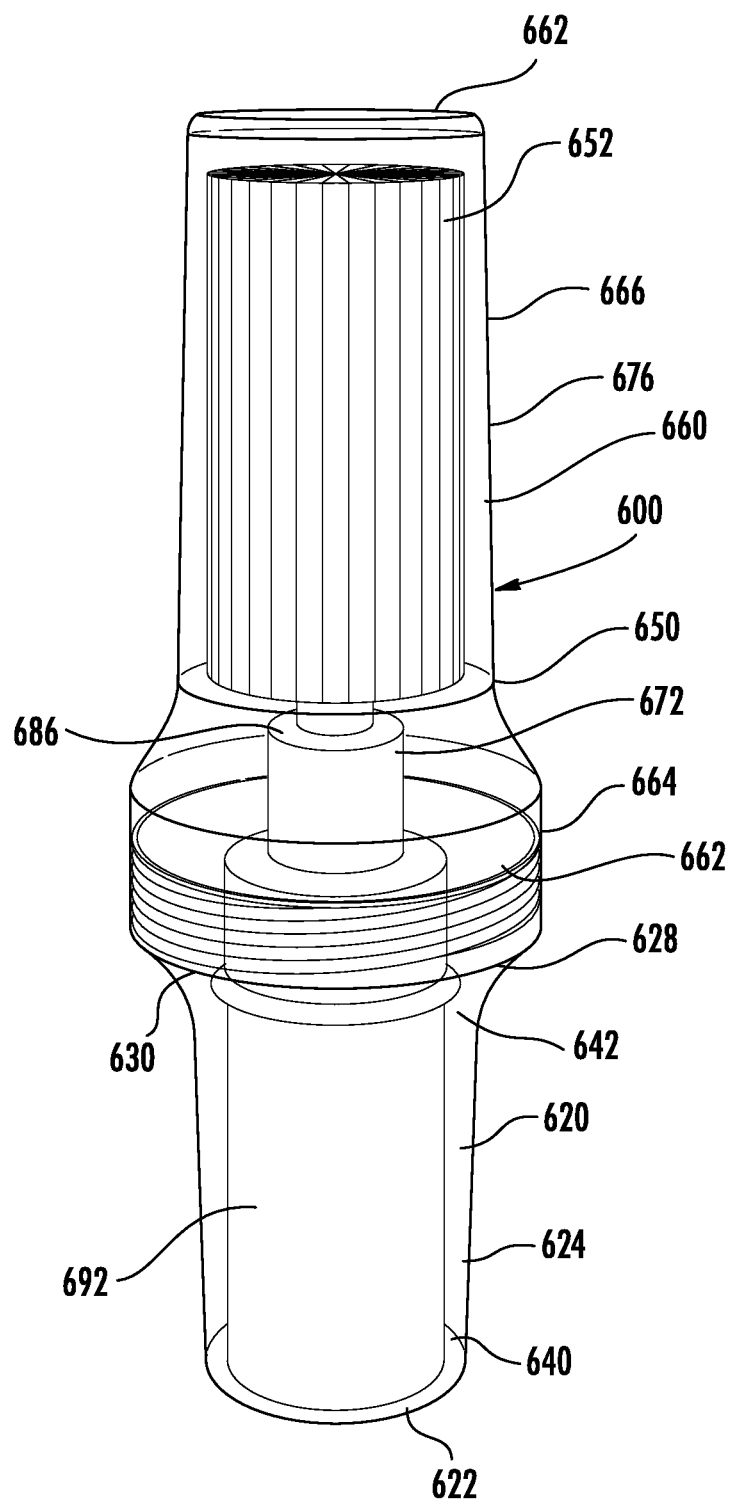
FIG. 10 is a perspective view of another embodiment of a urine sampling vessel.

FIGS. 1-4 show a biological sampling vessel 100. The urine sampling vessel 100 includes a container portion 120 and a sampling portion 150. As shown, the container portion 120 includes a body for housing sampled urine, and the sampling portion 150 is configured to both collect urine and close off the sampling vessel 100.

The container portion 120 includes a bottom wall 122 forming a base of the container portion, and a tubular sidewall 124 extending upward from the edges of the bottom wall 122. The bottom wall 122 and side wall 124 together define an interior 126 for housing a urine sample therein. The interior 126 is dimensioned to receive a wand 180 of the sampling portion 150, as described below.

The container portion 120 further includes an upper engagement portion 128, located at an upper end thereof, opposite the bottom wall 122. As shown, the upper engagement portion 128 includes a flared wall 130 that extends upward and outward from an upper edge of the side wall 124. A rim 132 extends upward from an upper edge of the flared wall 130 and includes a plurality of exterior threads 134 for engaging the sampling portion 150, as described below. An opening 144 leading to the interior 126 is formed at a top edge of the rim 132. A collar 136 may extend radially outward from the container portion 120 at the junction between the flared wall 130 and the rim 132.

A cylindrically shaped protrusion 138 may extend upwardly from the bottom wall 122, being located about a center point thereof and extending in a radial direction of the container portion 120. The side wall 124 may further include a lower annular ridge 140 extending radially inward from an inner surface thereof, and an upper annular ridge 142 extending radially inward from the inner surface thereof, being located at the junction between the side wall 124 and the flared wall 130 in the embodiment shown.

As shown in FIGS. 1-4 the sampling portion 150 includes a cap 160 and a wand 180. The cap 160 is dimensioned to cover the opening 144 of the container portion 120 and may form a moisture-tight sealed engagement with the container portion 120. The cap 160 includes a top wall 162 that covers the opening 144 when the container 120 is closed. A skirt 164 extends axially downward from an outer edge of the top wall 162. Interior threads 170 may be formed on an inner surface of the skirt 164. A ridge 166 may also be formed in the cap 160, extending upward between the outer edge of the top wall 162 and the skirt 164 and forming a groove 168 that extends upward from the bottom of the top wall 162. As shown, when the container 120 is closed, an upper portion of the rim 162 is housed within the groove 168, and the skirt 164 surrounds the outer surface of the rim 162. When the container 120 is closed, the exterior threads 134 of the rim 132 engage the interior threads 170 of the skirt 164 to retain the cap 160 over the opening 144.

The sampling portion 150 further includes a sampling wand 180. As shown, the wand 180 extends downward from a bottom surface of the top wall 162, and into the container 120 when in the closed position. The cap 160 of the embodiment shown includes a socket 172 for affixing the wand 180 to the cap 160. As shown, the wand 180 includes an elongate shaft 188 having a lower end 182 housed within the container 120 and an upper end 184 received by the socket 172. The socket 172 has a cylindrical shape, extends upward from the top wall 162 of the cap 160, and is dimensioned to snugly receive the upper end 184 of the shaft 188. A fastener may be provided to affix the upper end 184 within the socket 172 and in turn affix the wand to the cap 160. For example, the shaft 188 may include a tab 186 formed near the upper end thereof, and the socket 172 may include a plurality of circular ridges 174 on an inner surface thereof that engage the tab 186 to affix the upper end 184 within the socket.

The wand 180 further includes a sampling sponge assembly 190, which includes a sampling sponge 192 and a sponge holder 194 that holds the sponge in place upon the shaft 188. Referring to FIG. 1, the sponge holder 194 fits slidably around the shaft 188 and includes a sleeve 196 that fits around the shaft 188. A radially inwardly extending annular projection 200 is formed at an upper end of the sleeve 196, and the shaft 188 includes an upper annular groove 198 and a lower annular groove 212, each dimensioned to receive the projection to retain the sleeve 196 in a selected axial position on the shaft 188.

A cylindrical sponge housing 202 is formed extending outwardly and downwardly from the lower edge of the sleeve 196. The housing 202 is formed as a step, including a radially outwardly extending first wall 204 that forms a top surface of the housing 202, and a tubular axially extending second wall 206 that extends downward from the outer edge of the first wall 204. The sponge housing 202 retains an upper portion 234 of a sponge 192, as shown in FIG. 1. The first wall 204 and second wall 206 together form a housing space 208 that retains an upper portion of the sponge 192. A catch 210 extends radially outward from the second wall 206, about a bottom edge thereof.

The sponge 192 has a cylindrical shape with an axial passage 232 extending through the center thereof. When affixed in place by the sponge holder 194, the shaft 188 passes through the axial passage 232 and an upper portion 234 of the sponge 192 is held within the sponge housing 202. The outer diameter of the sponge 192 may be substantially equal to the inner diameter of the second wall 206, allowing the sponge 192 to be slightly compressed and fitted into the sponge housing 202 in this manner. As shown in FIG. 1, the inner diameter of the axial passage 232 is sufficient to allow passage of the shaft 188 therethrough. The bottom protrusion 138 may have an outer diameter slightly less than the inner diameter of the axial passage 232, allowing the protrusion 138 to sit within a bottom portion of the axial passage 232 when the container 120 is closed.

The vessel 100 is provided in the configuration of FIG. 1. As shown, the sampling portion 150 is engaged with the container 120, with the cap 160 being fitted over the container opening 144 and affixed thereon by way of engagement between exterior threads 134 and interior threads 170. The wand 180 extends into the interior 126 of the container 120. The sponge holder 194 at this point is located at a first, upward or retracted position on the shaft 188. The catch 210 of sponge holder 194 is located beneath the upper annular ridge 142 and the annular projection 200 of the sleeve 196 is held within the upper annular groove 198 of the shaft.

The vessel 100 is opened by first rotating the sampling portion 150 with respect to the container 120 to disengage the exterior threads 134 and interior threads 170. The sampling portion 150 is then drawn away from the container 120. As this occurs, the cap 160 is removed from the container 120, exposing the opening 144. At the same time, the engagement of catch 210 and annular ridge 142, as well as that of annular projection 200 and annular groove 198, retains the sponge holder 194 in place within the container interior 126, resulting in the annular projection 200 of the sleeve 196 becoming dislodged from the upper annular groove 198, and sliding of the sponge holder 194 on the shaft 188, down to a second, downward position on the shaft 188, shown in FIG. 2. As shown, once the sponge holder 194 reaches this extended position the annular projection 200 of sleeve 196 becomes positioned within the lower annular groove 212 of the shaft 188 to retain the sponge holder 194 in the second position. The sampling portion 150 continues to be drawn out from the container interior 126 until it exits the container 120 completely, at which point the catch 210 may snap inwardly and pass beneath the upper annular ridge 142, allowing the sponge holder 194 to be removed from the container 120.

Once the sampling portion 150 is removed from the container, a patient may use the sampling portion to obtain a urine sample by urinating on the sponge 192 until fully saturated with urine. The sampling portion 150 is then replaced on the container 120. When this occurs, the sponge 192, due to the sponge holder 194 being located in the second, downward axial position on the shaft 188, contacts the container bottom wall 122. As the wand 180 continues to be inserted into the container 120, the sponge becomes compressed between the first wall 204 of housing 202 and the container bottom wall 122, as shown in FIG. 3, causing the urine absorbed by the sponge to be expressed and contained within the container interior 126. Catch 210 snaps past the lower annular ridge 140 to help retain the sponge holder 194 in the second position on the shaft 188 and the sponge 192 in a compressed state. The cap 160 is then affixed to the container 120 by rotating to engage the exterior threads 134 with interior threads 170. The closed container may then be transported to a laboratory for analysis of the sampled urine. As shown in FIG. 4, the cap 160 may be removed from the container 120 for retrieving the urine sample for testing, leaving the sampling portion 150 in place within the container.

Another embodiment of a sampling wand 480 for use with a urine sampling vessel is shown in FIGS. 5-9. This sampling wand 480 is illustrated without a cap, but could be used with a cap such as that shown in FIGS. 1-4. Likewise, this sampling wand 480 could be used with a container such as that shown in FIGS. 1-4 and described above.

As shown, the wand 480 includes an elongate shaft 488 having a lower end foot 482 configured to be housed within a container and an upper end 484 configured to be affixed to a cap. The shaft 488 includes a tab 510 protruding from an outer surface thereof. The wand 480 further includes a sampling sponge assembly 490, which includes a sampling sponge 492 and a sponge compressor 494 that may compress the sponge 492. The sponge compressor 494 fits slidably around the shaft 488 and includes an elongate sleeve 496, a lower collar 498 and an upper collar 500, with the elongate sleeve 496 extending between the lower collar 498 and the upper collar 500. The sleeve 496 may define a plurality of apertures 508 distributed along the length thereof. The tab 510 fits through the apertures 508 to lock the sponge holder 494 at selected axial positions on the shaft 488.

The lower end foot 482's presence prevents dripping when placed in a container.

A sponge seat 502 formed as a radially outwardly extending wall is set at a fixed location on a lower portion of the shaft 488, below the sponge holder 494.

The sponge 492 has a cylindrical shape with an axial passage 532 extending through the center thereof. When affixed in place by the sponge holder 494, the shaft 488 passes through the axial passage 532 and the sponge 492 is retained on the shaft 488 between the lower collar 498 and sponge seat 502. The inner diameter of the axial passage 432 is sufficient to allow passage of the shaft 488 therethrough.

In use, this embodiment of the wand 480 is extracted from a container with the sponge in a compressed form, as shown in FIG. 5. A patient then urinates on the sponge 492 until fully saturated, which causes the sponge 492 to expand axially, until it extends to the full length between the lower collar 498 and sponge seat 502, as shown in FIG. 6. At this point, the sponge 492 may be dripping, making it inconvenient for the patient to replace the sampling portion on the container. The patient holds the sampling portion over a toilet and presses the upper collar 500 downward, urging the sponge holder 494 towards the lower collar 498, as shown in FIG. 7, until the tab 510 protrudes through one of the apertures 508, preventing further movement or signaling to the patient to stop applying pressure. This action compresses the sponge 492 slightly between the lower collar 498 and sponge seat 502, causing a small amount of the urine that was absorbed to be expressed. The patient may then release pressure on the upper collar 500, which may result in the sponge holder 494 returning to its original position on the shaft 488. The sampling assembly 150 may then be replaced on the container, the container closed and transported to a laboratory for analysis. Once the container is received at the laboratory, a technician may, prior to fully removing the sampling portion 150, again press downward on the upper collar 500, this time pressing until the tab 510 snaps past the opening 508, until the sponge holder 494 is in a second, lower position, as shown in FIG. 8, causing the urine that has been absorbed by the sponge 492 to be expressed into the container for analysis. The technician may then release pressure on the upper collar 500, allowing the sponge holder 494 to return to its original position and the sponge to re-expand, as shown in FIG. 9.

Figure 11:
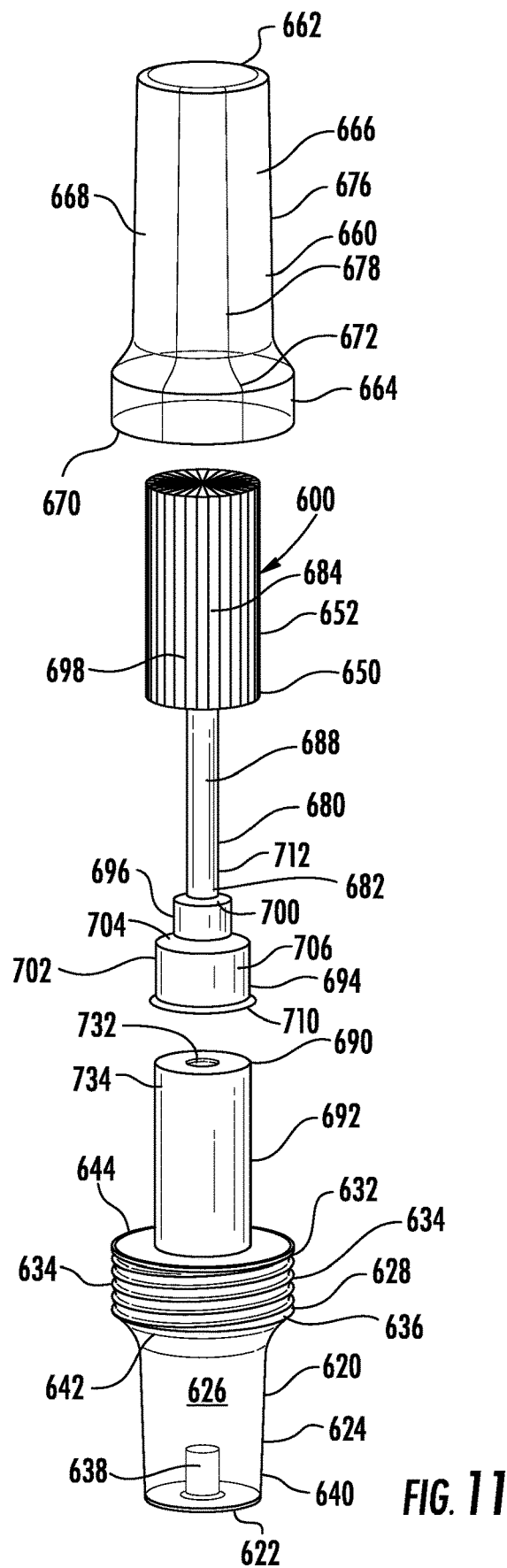
FIG. 11 is an exploded view of the vessel of FIG. 10.

FIGS. 10 and 11 show another embodiment of a urine sampling vessel 600. The urine sampling vessel 600 includes a container portion 620 and a sampling portion 650. As shown, the container portion 620 includes a body suitable for housing sampled urine, and the sampling portion 650 is configured to both collect urine and close off the sampling vessel 600, as described in detail below.

The container portion 620 of this embodiment includes a bottom wall 622 forming a base of the container portion, and a tubular sidewall 624 extending upward from the edges of the bottom wall 622. The bottom wall 622 and side wall 624 together define an interior 626 for housing a urine sample therein. The interior 626 is dimensioned to receive a wand 680 of the sampling portion 650, as described below.

The container portion 620 further includes an upper engagement portion 628, located at an upper end thereof, opposite the bottom wall 622. As shown, the upper engagement portion 628 includes a flared wall 630 that extends upward and outward from an upper edge of the side wall 624. A rim 632 extends upward from an upper edge of the flared wall 630 and includes a plurality of exterior threads 634 for engaging the sampling portion 650, as described below. An opening 644 leading to the interior 626 is formed at a top edge of the rim 632. A collar 636 may extend radially outward from the container portion 620 at the junction between the flared wall 630 and the rim 632.

A cylindrically shaped protrusion 638 may extend upwardly from the bottom wall 622, being located about a center point thereof and extending in a radial direction of the container portion 620. The side wall 624 may further include a lower annular ridge 640 extending radially inward from an inner surface thereof, and an upper annular ridge 642 extending radially inward from the inner surface thereof, being located at the junction between the side wall 624 and the flared wall 630 in the embodiment shown.

Referring to FIG. 11, the sampling portion 650 is shown in detail. As shown, the sampling portion 650 includes a cap 660 and a wand 680. The cap 660 is dimensioned to cover the opening 644 of the container portion 620 and may form a moisture-tight sealed engagement with the container portion 620. The cap 660 of this embodiment includes an upper housing 666 defined by a top wall 662 and downwardly depending tubular side wall 676. A skirt 664 extends axially downward from a lower edge of the side wall 676. Interior threads 670 may be formed on an inner surface of the skirt 664. An inner tubular wall 678 extends downward from the top wall 662, within and surrounded by the side wall 676, such that an annular chamber 668 is defined between the two. The chamber 668 of this embodiment houses a plurality of test strips 652, such as a 12 panel POC test strip that may be used to test a urine sample housed within the vessel 600 on site to get preliminary test results by inverting urine contacts the test strips 652.

As shown in FIG. 10, when the container 620 is closed, an upper portion of the rim 662 is housed within the chamber 668, and the skirt 664 surrounds the outer surface of the rim 662. When the container 620 is closed, the exterior threads 634 of the rim 632 engage the interior threads 670 of the skirt 664 to retain the cap 660 over the opening 644 and prevent leakage. To further prevent leakage, there may be annular seals between the container 620 and cap 660.

The sampling portion 650 further includes a sampling wand 680. As shown, the wand 680 extends downward from the cap 660, and into the container 620 when in the closed position. The cap 660 of the embodiment shown includes a socket 672 formed as a bottom portion of inner tubular wall 678, and configured for affixing the wand 680 to the cap 660. As shown, the wand 680 includes an elongate shaft 688 having a lower end 682 housed within the container 620 and an upper end 684 received by the socket 672. The socket 672 has a substantially cylindrical shape, and is dimensioned to snugly receive the upper end 684 of the shaft 688. A fastener may be provided to affix the upper end 684 within the socket 672 and in turn affix the wand 680 to the cap 660. For example, the shaft 688 could include an outer thread 686 formed near the upper end thereof, and the socket 672 could include an inner thread 672 that engages the outer thread 686 to affix the upper end 684 within the socket.

The wand 680 further includes a sampling sponge assembly 690, which includes a sampling sponge 692 and a sponge holder 694 that holds the sponge 692 in place upon the shaft 688. The sponge holder 694 fits slidably around the shaft 688 and includes a sleeve 696 that fits around the shaft 688. A radially inwardly extending annular projection 700 is formed at an upper end of the sleeve 696, and the shaft 688 includes an upper annular groove 698 and a lower annular groove 712, each dimensioned to receive the projection to retain the sleeve 696 in a selected axial position on the shaft 688.

A cylindrical sponge housing 702 is formed extending outwardly and downwardly from the lower edge of the sleeve 696. The housing 702 is formed as a step, including a radially outwardly extending first wall 704 that forms a top surface of the housing 702, and a tubular axially extending second wall 706 that extends downward from the outer edge of the first wall 704. The sponge housing 702 retains an upper portion 734 of a sponge 692. The first wall 704 and second wall 706 together form a housing space 708 that retains an upper portion of the sponge 692. A catch 710 extends radially outward from the second wall 706, about a bottom edge thereof.

The sponge 692, as shown in detail in FIG. 11, has a cylindrical shape with an axial passage 732 extending through the center thereof. When affixed in place by the sponge holder 694, the shaft 688 passes through the axial passage 732 and an upper portion 634 of the sponge 692 is held within the sponge housing 702. The outer diameter of the sponge 692 may be substantially equal to the inner diameter of the second wall 706, allowing the sponge 692 to be slightly compressed and fitted into the sponge housing 702 in this manner. The inner diameter of the axial passage 732 is sufficient to allow passage of the shaft 688 therethrough. The bottom protrusion 638 may have an outer diameter slightly less than the inner diameter of the axial passage 732, allowing the protrusion 638 to sit within a bottom portion of the axial passage 732 when the container 620 is closed.

The vessel 600 is provided with the cap 660 being fitted over the container opening 644 and affixed thereon by way of engagement between exterior threads 634 and interior threads 670. The wand 680 extends into the interior 626 of the container 620. The sponge holder 694 at this point is located at a first, upward position on the shaft 688 at this stage, similar to that shown in FIG. 1. The catch 710 of sponge holder 694 is located beneath the upper annular ridge 642 and the annular projection 700 of the sleeve 696 is held within the upper annular groove 698 of the shaft.

The vessel 600 is opened by first rotating the sampling portion 650 with respect to the container 620 to disengage the exterior threads 634 and interior threads 670. The sampling portion 650 is then drawn away from the container 620. As this occurs, the cap 660 is removed from the container 620, exposing the opening 644. At the same time, the engagement of catch 710 and annular ridge 642, as well as that of annular projection 700 and annular groove 698, retains the sponge holder 694 in place within the container interior 626, resulting in the annular projection 700 of the sleeve 696 becoming dislodged from the upper annular groove 698, and sliding of the sponge holder 694 on the shaft 688, down to a second, downward position on the shaft 688, similar to that shown in FIG. 2. Once the sponge holder 694 reaches this position the annular projection 700 of sleeve 696 becomes positioned within the lower annular groove 712 of the shaft 688 to retain the sponge holder 694 in the second position. The sampling portion 650 continues to be drawn out from the container interior 626 until it exits the container 620 completely, at which point the catch 710 may snap inwardly and pass beneath the upper annular ridge 642, allowing the sponge holder 694 to be removed from the container 620.

Once the sampling portion 650 is removed from the container 620, a patient may use the sampling portion to obtain a urine sample by urinating on the sponge 692 until fully saturated with urine. The sampling portion 650 is then replaced on the container 620. When this occurs, the sponge 692, due to the sponge holder 694 being located in the second, downward axial position on the shaft 688, contacts the container bottom wall 622. As the wand 680 continues to be inserted into the container 620, the sponge becomes compressed between the first wall 704 of housing 702 and the container bottom wall 622, causing the urine absorbed by the sponge to be expressed and contained within the container interior 626. Catch 710 snaps past the lower annular ridge 640 to help retain the sponge holder 694 in the second position on the shaft 688 and the sponge 692 in a compressed state. The cap 660 is then affixed to the container 620 by rotating to engage the exterior threads 634 with interior threads 670. The closed container may then be transported to a laboratory for analysis of the sampled urine.

FIGS. 12-16 show another embodiment of a urine sampling vessel 800. The urine sampling vessel 800 includes a container portion 820 and a sampling portion 850. As shown, the container portion 820 includes a body suitable for housing sampled urine, and the sampling portion 850 is configured to both collect urine and close off the sampling vessel 800, as described in detail below.

The container portion 820 includes a bottom wall 822 forming a base of the container portion 820, and a tubular sidewall 824 extending upward from the edges of the bottom wall 822. The bottom wall 822 and side wall 824 together define an interior for housing a urine sample therein. The interior 826 is dimensioned to receive a wand 880 of the sampling portion 850, as described below.

The container portion 820 further includes an upper engagement portion 828, located at an upper end thereof, opposite the bottom wall 822. As shown, the upper engagement portion 828 includes a plurality of interior threads 834 for engaging the sampling portion 850, as described below. An opening 844 leading to the interior is formed at a top edge side wall 824.

Figure 13:
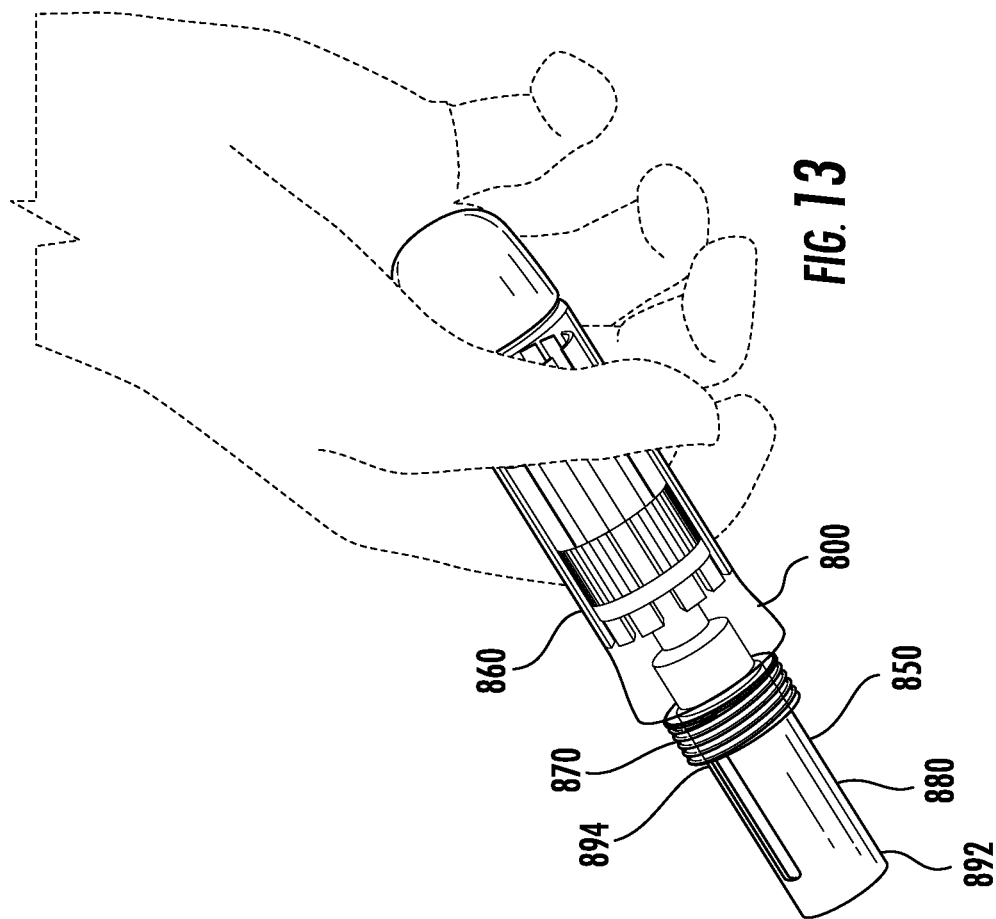
FIG. 13 is a perspective view of the vessel of FIG. 12, in an opened position and during the process of obtaining a urine sample.
Figure 12:
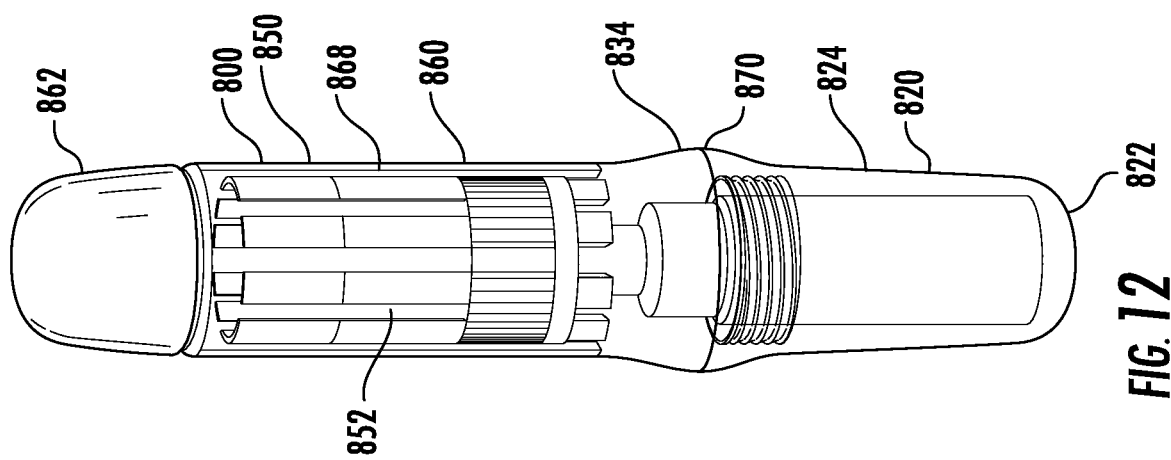
FIG. 12 is a perspective view of another embodiment of a urine sampling vessel.
Figure 14:
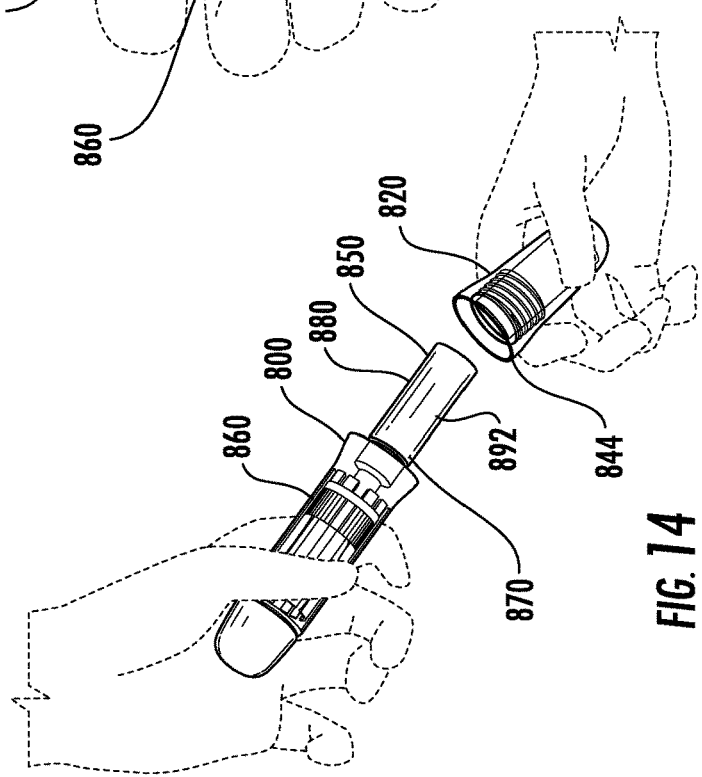
FIG. 14 is a perspective view of the vessel of FIG. 12, after use obtaining a urine sample and during the reclosing process.

Referring to FIGS. 12-14, the sampling portion 850 includes a cap 860 and a wand 880. The cap 860 is dimensioned to cover the opening 844 of the container portion 820 and may form a moisture-tight sealed engagement with the container portion 820. The cap 860 includes a button 862 forms a top surface of the cap 860 and a tubular side wall 876 that extends downward from the outer edges of the button 862. Exterior threads 870 may be formed on an outer surface of the side wall 876, near the bottom edge thereof. As shown, when the container 820 is closed, the interior threads 834 engage the exterior threads 870 to retain the cap 860 over the opening 844. The outer surfaces of sampling portion side wall 876 and container portion side wall 824 may be flush, and the entire shape of the vessel 800 may have an elongate extension, similar to that of a pen, so as to provide for convenient handling and transport of the vessel 800.

The sampling portion 850 further includes a sampling wand 880. As shown, the wand 880 extends downward from a bottom surface of the button 862, past side wall 876, and into the container 820 when in the closed position. An annular chamber 868 for housing a plurality of test strips 852 may be defined between the wand 880 and the side wall 876.

Figure 15:
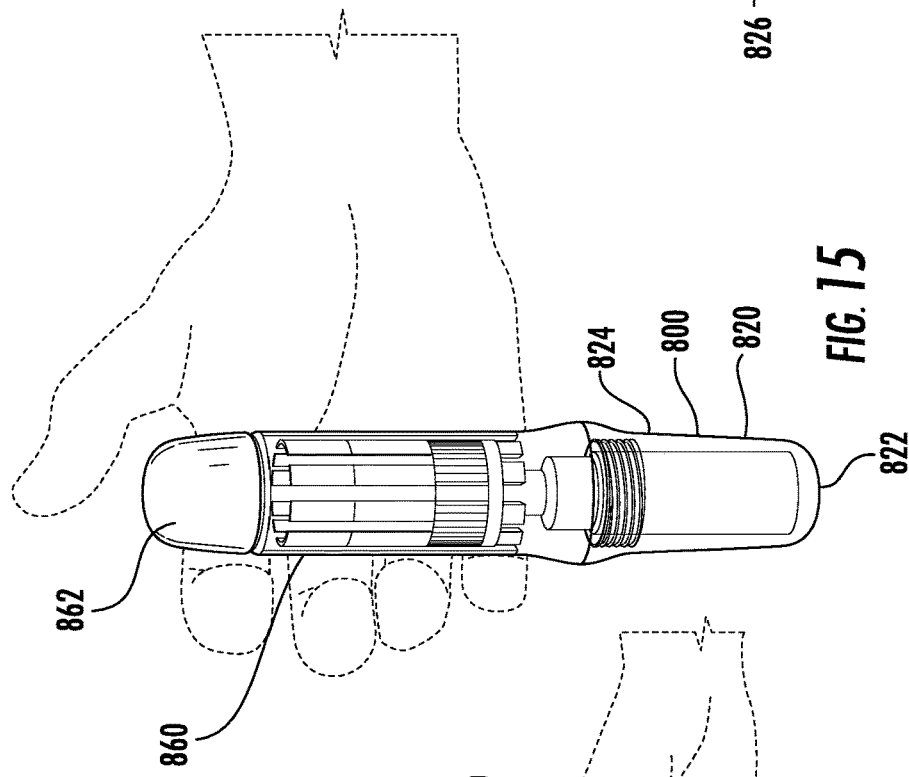
FIG. 15 is a perspective view of the vessel of FIG. 12, in a closed position and after the button has been depressed to move the sponge into a retracted position.

The wand 880 includes a sampling sponge assembly 890, which includes a sampling sponge 892 and a sponge holder 894 that holds the sponge 892 in place. The sponge holder 894 is formed as a shaft that extends downward from the button 862, and the sponge 892 extends further downward from an end of the sponge holder 894, into the container 820 when closed. The button 862, being coupled with the sponge holder 894, may be actuated to move the entire wand 880 between a first, extended position, as shown in FIG. 12, and a second, retracted position, as shown in FIG. 15.

The vessel 800 is provided in the configuration of FIG. 12. As shown, the sampling portion 850 is engaged with the container 820, with the cap 860 being fitted over the container opening 844 and affixed thereon by way of engagement between interior threads 834 and exterior threads 870. The wand 880 is in a first, extended position and extends into the interior 826 of the container 820.

Figure 16:
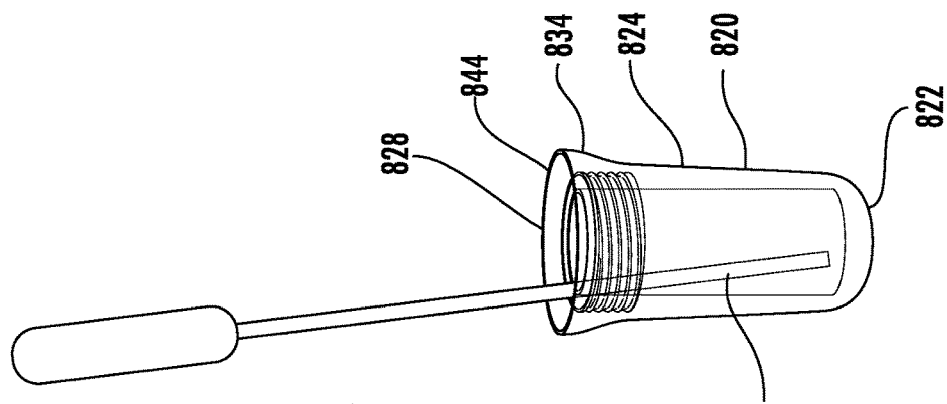
FIG. 16 is a perspective view of the container of the urine sampling vessel of FIG. 12, with a pipette inserted to retrieve a urine sample contained therein.

The vessel 800 is opened by first rotating the sampling portion 850 with respect to the container 820 to disengage the interior threads 834 and exterior threads 870. The sampling portion 850 is then removed from the container 820. A patient may use the sampling portion to obtain a urine sample by urinating on the sponge 892 until fully saturated with urine, as shown in FIG. 13. The sampling portion 850 is then replaced on the container 820, as shown in FIG. 14 and rotated with respect to the container 820 to engage interior threads 834 with exterior threads 870. The patient may then actuate the button 862, resulting in the wand 880 retracting from its first, extended position, to a second retracted position, shown in FIG. 15. As shown, the sponge 892 and, in turn, the urine sample contained therein come into contact with the test strips 852 for analysis of the urine sample. In another embodiment, actuation of the button 862 may be used to express the urine sample from the sponge into the container 820. The vessel 800 may be transported to a laboratory and the urine sample removed from the container for analysis using a pipette, as shown in FIG. 16. In another embodiment, the patient or an accessioner may test the urine sample by inserting one of the test strips 852 into the container 820.

Figure 18:
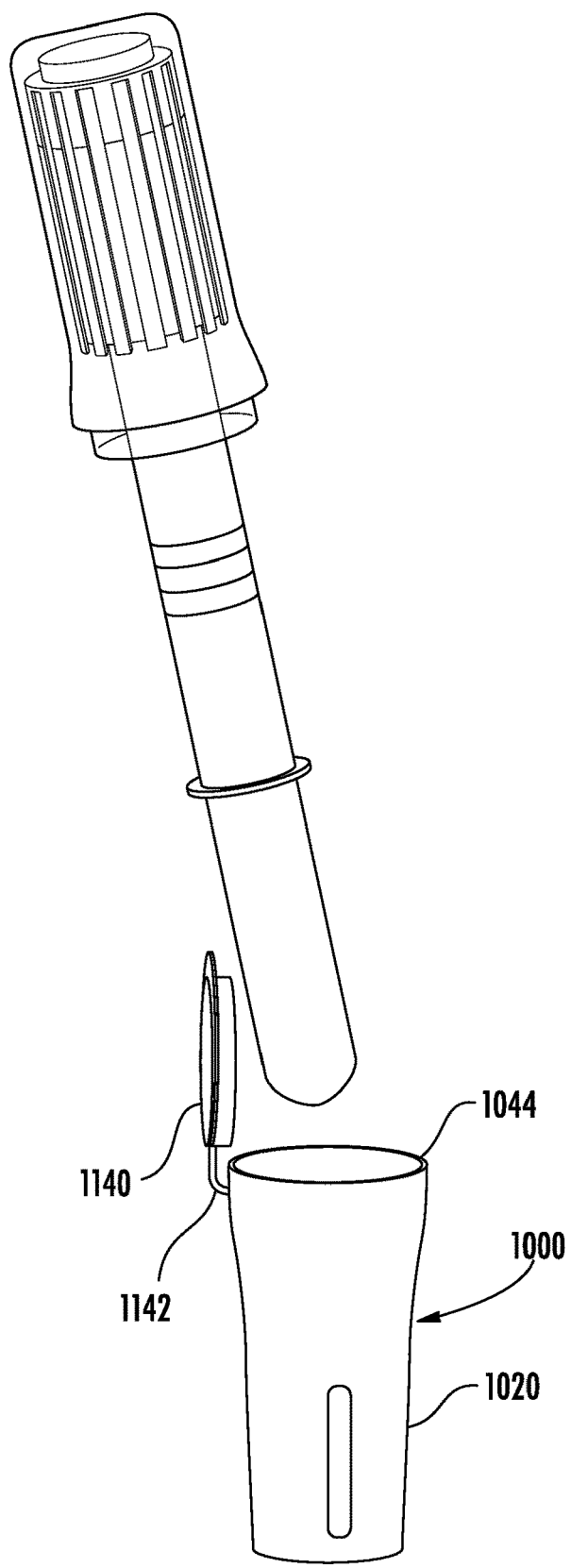
FIG. 18 is a perspective view of the urine sampling vessel of FIG. 17, in an opened position.

Another embodiment of a vessel 1000 is shown in FIGS. 17-19. The vessel 1000 of this embodiment is similar to that shown in FIGS. 12-16, but further includes a transport lid 1140. The transport lid is affixed to the container 1020 by a tether 1142 in the embodiment shown, and is configured to cover the opening 1044 when the cap 1060 is not affixed to the container 1020. The transport lid 1140 may engage the container 1020 to form a moisture tight seal for transport of the container 1020 when containing a urine sample.

FIGS. 20A and 20B show alternate embodiments of the wands 2010 and 2050. Each wand has a ribbed, bulbous shaped handle 2020 and absorbent sponge 2040 that collects a sample. The handle 2020's shape as flared and ribs prevents urine egress up the handle to a user's hands. The difference between the wands 2010 and 2050 is the inclusion of the foot 2060 that prevents dripping similar to the foot 482 discussed earlier, as opposed to the wand 2010 that has a section 2030 that terminates at or before the end of the sponge 2040.

The container, wand, and cap portions of any embodiment of the vessel described herein can be made of any suitable material known in the art, such as a polymeric material. Alternatively, certain components, such as the wand, could be formed of a compostable material such as wood, cardboard, or other cellulosic materials. Any of the sponges herein can be made of various types of absorbent foam materials, for example: natural sponges, cellulosic sponges, or hydrophilic polymeric materials, polyurethane foam as well as absorbent textile materials such as wool, cotton or absorbent polymeric textiles.

Figure 21:
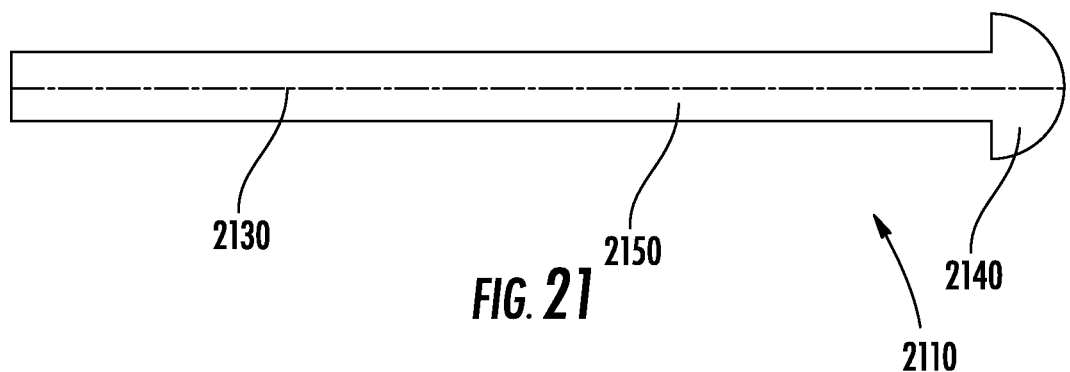
FIGS. 21-24 show another embodiment of the wand.
Figure 22:
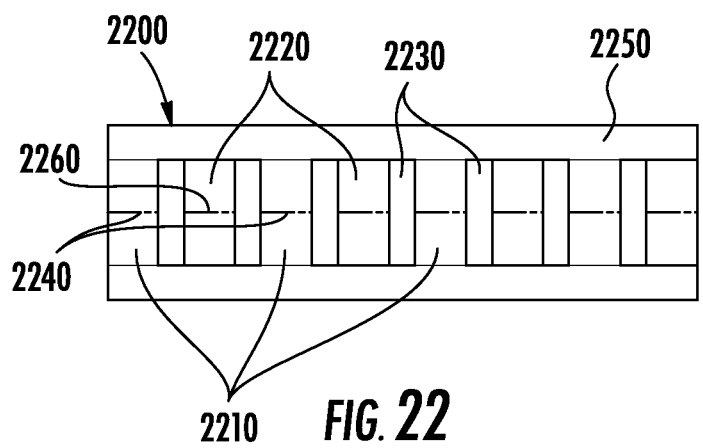
Figure 23:
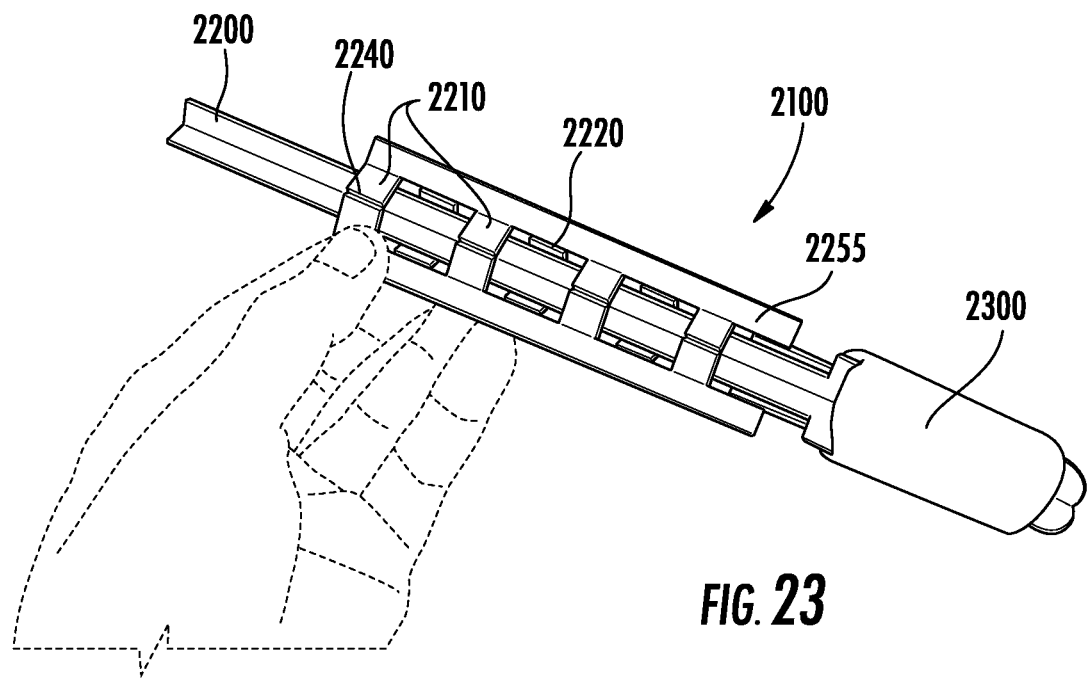
Figure 24:
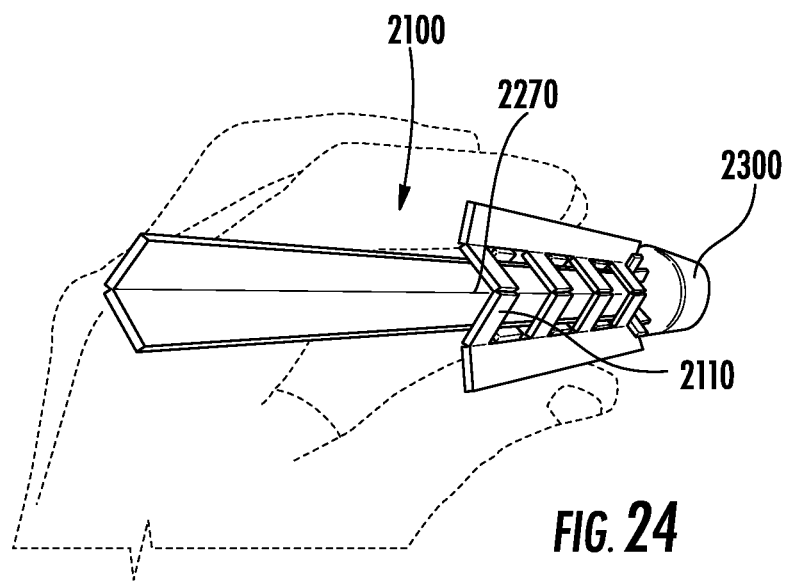

FIGS. 21-24 show another sample collection wand 2100, in this case using a compostable, flat, or recyclable construction. As shown, the wand 2100 comprises two pieces, a shaft 2110 and body 2200, both of which may be formed as flat as shown in FIGS. 21 and 22. The shaft 2110 may be formed prescored along shaft score 2130 and include an enlarged head portion 2140 separate from an elongated portion 2150.

The body 2200 has engagement tabs 2210, 2220 separated by gaps 2230. Engagement tabs 2210 may be scored along scores 2240 on a body portion side 2250 facing the viewer, and the engagement tabs 2220 may be scored along scored 2260 on a body portion side 2255 facing away from the viewer.

When folded along the scores, the body may form a roughly square sectioned channel 2270 therethrough to engage the shaft 2110 and form the wand once the sponge 2300 is secured to the head portion 2140, which may extend through a hole in the sponge 2300. In use, a user holds the body 2200 in his hand while collecting the sample.

The absorbent material described may be made from absorbent material, preferably a material that is absorbent under a stream but not inclined to drip. The materials that have been found to perform under these conditions are hydrophilic polyurethane foam, cellulose sponge, and melamine foam.

While the invention has been described with reference to the embodiments above, a person of ordinary skill in the art would understand that various changes or modifications may be made thereto without departing from the scope of the claims.

We claim:
1. A urine sampling vessel, comprising:
  a container portion having an opening and an interior for containing a urine sample, the container portion having container portion threads; and
  a sampling portion that removably engages the container portion in a threaded engagement to close off the interior, the sampling portion having sampling portion threads, the sampling portion comprising a sampling wand having a sampling sponge engaged thereto, wherein when the sample portion and the container portion engage with each other in two different positions, a first pre-use position in which the sampling sponge is not compressed and a second post-use position in which the sampling sponge is compressed, wherein in the second post-use position, the sampling sponge, when used to collect a urine sample, compresses the sampling sponge and expresses the urine sample into the container portion, wherein in both the pre-use position and post-use position, the container portion threads and sampling portion threads are fully engaged to one another;
  wherein the wand comprises a shaft and a sponge holder that holds the sampling sponge;
  wherein sampling portion further comprises a cap and the shaft is fixed to the cap;

wherein the sponge holder is engaged to the shaft and moves with respect thereto;

wherein the sponge holder moves between a retracted position closer to the cap to an extended position further from the cap.

2. The urine sampling vessel of claim 1, wherein the sampling portion engages the container portion to form a moisture-tight seal.

3. The urine sampling vessel of claim 1, wherein the sponge holder engages an upper portion of the sampling sponge around a perimeter of the sampling sponge in a compression fit.

4. The urine sampling vessel of claim 1, wherein the sampling sponge is made from a material comprising hydrophilic polyurethane foam.

5. The urine sampling vessel of claim 1, wherein the sampling sponge is made from a material comprising cellulose sponge.

6. The urine sampling vessel of claim 1, wherein the sampling sponge is made from a material comprising melamine foam.

7. The urine sampling vessel of claim 1, wherein the container portion, sampling portion, and sampling sponge share a common axis therethrough.

8. The urine sampling vessel of claim 7, wherein a shaft extends along the common axis and is engaged with both the sponge to the sampling portion.

* * * * *